(12) United States Patent
Williams et al.

(10) Patent No.: US 7,132,663 B2
(45) Date of Patent: Nov. 7, 2006

(54) METHODS AND APPARATUS FOR REAL-TIME ERROR CORRECTION

(75) Inventors: John Jay Williams, Hartland, WI (US); David Leo McDaniel, Dousman, WI (US)

(73) Assignee: General Electric Company, Schenectady, NY (US)

( * ) Notice: Subject to any disclaimer, the term of this patent is extended or adjusted under 35 U.S.C. 154(b) by 141 days.

(21) Appl. No.: 10/981,915

(22) Filed: Nov. 4, 2004

(65) Prior Publication Data

US 2006/0091314 A1    May 4, 2006

(51) Int. Cl.
*G01T 1/164* (2006.01)
(52) U.S. Cl. .............................. 250/363.03; 250/363.07
(58) Field of Classification Search ........... 250/363.03, 250/363.07
See application file for complete search history.

(56) References Cited

U.S. PATENT DOCUMENTS

| | | | |
|---|---|---|---|
| 4,058,728 A * | 11/1977 | Nickles ...................... | 250/369 |
| 4,599,690 A * | 7/1986 | Stoub ...................... | 250/363.07 |
| 4,931,968 A * | 6/1990 | Hirose .................... | 250/363.07 |
| 5,241,181 A | 8/1993 | Mertens et al. | |
| 5,272,343 A | 12/1993 | Stearns | |
| 5,272,344 A | 12/1993 | Williams | |
| 5,300,782 A | 4/1994 | Johnston et al. | |
| 5,543,622 A | 8/1996 | Stearns | |
| 5,585,637 A | 12/1996 | Bertelsen et al. | |
| 5,900,636 A * | 5/1999 | Nellemann et al. .... | 250/363.04 |
| 5,999,588 A | 12/1999 | Shao et al. | |
| 6,008,493 A | 12/1999 | Shao et al. | |
| 6,198,104 B1 * | 3/2001 | Geagan et al. ......... | 250/363.04 |
| 6,232,604 B1 | 5/2001 | McDaniel et al. | |
| 6,403,960 B1 | 6/2002 | Wellnitz et al. | |
| 6,410,919 B1 * | 6/2002 | Nickles ................. | 250/363.03 |
| 6,410,920 B1 | 6/2002 | Shao et al. | |
| 6,590,957 B1 | 7/2003 | Warburton et al. | |
| 2002/0179843 A1 * | 12/2002 | Tanaka et al. ......... | 250/363.03 |

* cited by examiner

*Primary Examiner*—Albert Gagliardi
(74) *Attorney, Agent, or Firm*—Small Patent Law Group; Dean D. Small

(57) ABSTRACT

Methods and apparatus for correcting for at least one of deadtime losses and random coincidences in a positron emission tomography (PET) medical imaging device having a plurality of detectors at successive locations circumferentially spaced about a viewing area, the method comprising, receiving signals indicative of positron-electron annihilation events occurring along a line of response between pairs of detectors for a plurality of predetermined time segments of data acquisition of the events, calculating a correction sinogram for each predetermined time segment from data acquired during each respective single time segment, calculating corrected counts in the correction sinogram for each time segment, calculating a time-weighted correction sinogram for each time segment, combining the time-weighted correction sinogram to generate an acquisition sinogram, and generating an image from the acquisition sinogram.

24 Claims, 2 Drawing Sheets

METHODS AND APPARATUS FOR REAL-TIME ERROR CORRECTION

BACKGROUND OF THE INVENTION

This invention relates generally to positron emission tomography (PET) scanners, and more particularly to methods and apparatus for correcting errors during data image reconstruction.

Positrons are positively charged electrons which are emitted by radionuclides that have been prepared using a cyclotron or other device. The radionuclides are employed as radioactive tracers called "radiopharmaceuticals" by incorporating them into substances that are injected into the patient and become involved in such processes as glucose metabolism, fatty acid metabolism and protein synthesis.

As the radionuclides decay, they emit positrons. The positrons travel a very short distance before they encounter an electron, and when this occurs, they are annihilated and converted into two photons, or gamma rays. This annihilation event is characterized by two features which are pertinent to PET scanners: each gamma ray has an energy of 511 keV and the two gamma rays are directed in substantially opposite directions. An image is created by determining the number of such annihilation events at each location within the field of view.

The PET scanner includes one or more rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events indicates the number of positron annihilations that occurred along a line joining the two opposing detectors. Within a few minutes hundreds of millions of events are recorded to indicate the number of annihilations along lines joining pairs of detectors in the ring. These numbers are employed to reconstruct an image using well known computed tomography techniques.

However, during an acquisition period there are several sources of annihilation detection error. Two of the more prominent sources of detection error are referred to as "deadtime" and "randoms." The phenomenon known as deadtime occurs when two photons impact a single crystal at essentially the same time so that while the first of the photons is being processed by the detector unit a second of the photons is ignored by the unit. In these cases, at least one of the annihilations is not recognized and that annihilation data is lost for the purposes of image reconstruction.

The phenomenon known as randoms occurs when photons from two different annihilations are detected by two crystals at essentially the same time. Randoms are due to valid events being detected at the same time even though they did not originate from the same annihilation. The valid events may also come from other non-annihilation sources. These events are called randoms because it is random chance that the two arrived at the same time. The probability of such a random event occurring is directly proportional to the event rate in the two single detectors compared in the coincidence pair. Hence the interest in measuring singles to calculate the correction. Data is not lost when a random occurs, rather an event is recorded that should be later removed to give an accurate representation of the true source.

In order to facilitate minimizing the number of random coincidences and the effects of deadtime, the size of the coincidence window may be selected to be as small as possible. The coincidence window width affects the randoms rate. Deadtime is determined by single event processing time. PET systems typically have the capability to measure deadtime losses in their current counting functions. However, because the measured value is collected once per data frame, changes in loss rates during a single frame cannot be corrected for. In addition, the singles events rates are recorded in order to provide a means to correct the number of randoms events in the acquisition. Such changes in losses can occur when either the patient activity changes substantially (such as gated cardiac with bolus injection) or when the local external source changes with time (such as a rotating transmission source).

BRIEF DESCRIPTION OF THE INVENTION

In one embodiment a method of correcting for at least one of deadtime losses and random coincidences in a positron emission tomography (PET) medical imaging device having a plurality of detectors at successive locations circumferentially spaced about a viewing area, the method comprising, receiving signals indicative of positron-electron annihilation events occurring along a line of response between pairs of detectors for a plurality of predetermined time segments of data acquisition of the events, calculating a correction sinogram for each predetermined time segment from data acquired during each respective single time segment, calculating corrected counts in the correction sinogram for each time segment, calculating a time-weighted correction sinogram for each time segment, combining the time-weighted correction sinogram to generate an acquisition sinogram, and generating an image from the acquisition sinogram.

In another embodiment, a positron emission system is provided. The system includes a positron emission tomography scanner, at least one pair of opposing detectors spaced about a scanner viewing area, a controller for controlling the operation of the positron emission tomography scanner, said controller configured to, acquire image data with at least one of inherent deadtime losses and random coincidences during a predetermined time segment using a plurality of channels, and process the acquired image data during dead time periods, said process including, calculating a correction sinogram for each predetermined time segment from data acquired during each respective single time segment, calculating corrected counts in the correction sinogram for each time segment, calculating a time-weighted correction sinogram for each time segment, combining the time-weighted correction sinogram to generate an acquisition sinogram, and generating an image from the acquisition sinogram.

In yet another embodiment, a computer program for controlling a positron emission tomography (PET) system is provided. The program includes a code segment that is configured to control the PET system to reduce at least one of deadtime losses and random coincidence errors by calculating a time-weighted correction sinogram for each time segment of a detector channel of the positron emission system, said computer program, receives emission data indicative of positron electron annihilation events during a predetermined time segment, calculates a correction sinogram for each predetermined time segment from data acquired during each respective single time segment, calculates corrected counts in the correction sinogram for each time segment, calculates a time-weighted correction sinogram for each time segment, combines the time-weighted correction sinogram to generate an acquisition sinogram, and generates an image from the acquisition sinogram.

DETAILED DESCRIPTION OF THE INVENTION

Figure 1:
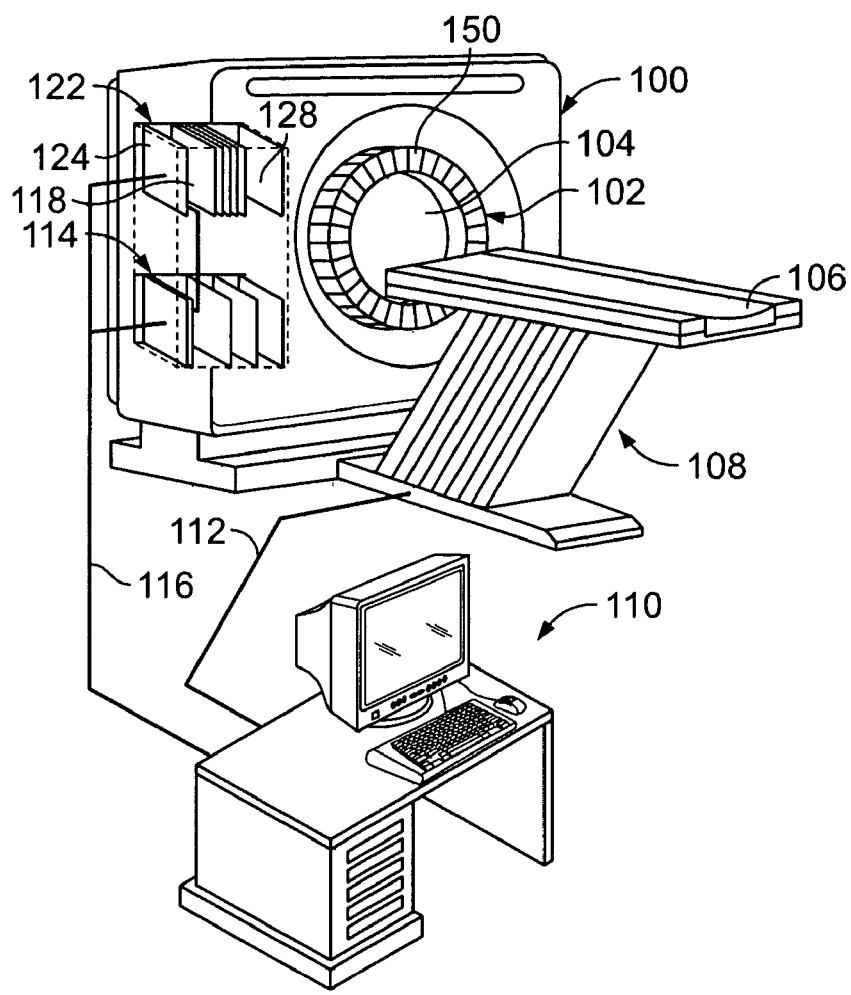
FIG. 1 is a perspective view of an exemplary PET scanner system.

FIG. 1 is a perspective view of an exemplary PET scanner system that includes a gantry 100 which supports a detector ring assembly 102 about a central axis, or bore 104. A patient table 108 is positioned adjacent gantry 100 and is aligned with the central axis of the bore 104. A patient table controller (not shown) moves the table bed 106 into the bore 104 in response to commands received from an operator work station 110 through a serial communications link 112. A gantry controller 114 is mounted within the gantry 100 and is responsive to commands received from the operator work station 110 through a second serial communication link 116 to operate the gantry 100. For example, the gantry 100 can perform a "transmission scan" with a calibrated radionuclide source to acquire attenuation measurements, or it can perform a normal scan, in which positron annihilation events are counted and an image is reconstructed.

Figure 2:
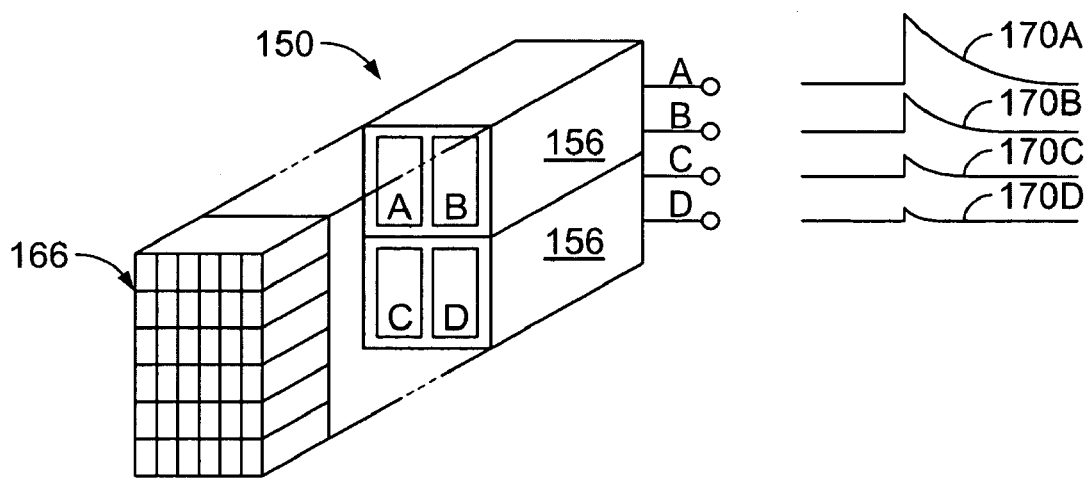
FIG. 2 is a perspective view of a detector module which may be used with the PET scanner system shown in FIG. 1.

Detector ring 102 may include a plurality of detector modules as shown in FIG. 2, each module containing, for example, eight detector blocks 150. In the exemplary embodiment, each block 150 includes a set of thirty-six scintillator crystals 166 arranged in a 6 by 6 matrix and disposed in front of four anode photomultiplier tube (PMT) 156. Each anode 156 produces an analog signal 170A–170D, which rises sharply when a scintillation event occurs, and then tails off exponentially. The relative magnitudes of the analog signals 170A–170D is determined by the position in the 6 by 6 scintillator matrix at which the scintillation event took place. The total magnitude of these signals is determined by the energy of the gamma ray which caused the scintillation event.

An event processor 122 consisting of acquisition circuits 118, coincidence detector 124, and acquisition CPU 128 is mounted within the gantry 100. The acquisition circuit 118 receives the four signals 170A–170D from each of the blocks 150 in detector ring 102. Acquisition circuits 118 determine the event coordinates within the block of scintillating crystals 166 by comparing the relative signal strengths as follows:

$x=(170A+170C)/(170A+170B+170C+170D)$, and $z=(170A+170B)/(170A+170B+170C+170D)$ Coordinates (x,z), along with the sum of all four signals (170A+170B+170C+170D) are digitized and the digital values summed in accumulators to give the integrated values of the signals. Each acquisition circuit 118 also produces an event detection pulse (EDP) which indicates substantially the exact moment the scintillation event took place. The processor 122 has an acquisition CPU 128 which controls communications and links the processor 122 to the local area network 116. The acquisition circuits 118 synchronize the event with the operation of the coincidence detector 124 by detecting the event pulse (EDP), and converting it into an 8-bit time marker which indicates when within the current time sample period the scintillation event took place. Also, this circuit 118 discards any detected events if the total energy of the scintillation is outside a pre-determined range about 511 keV (for example plus or minus about 0.20%). During each time sample period, the information from each of the plurality of detector modules is assembled into a set of digital numbers that indicate precisely when an event took place and the position of scintillating crystal 166 which detected the event. This event data packet is conveyed as a stream to the coincidence detector 124.

Typical PET imaging systems collect deadtime loss data and singles event rates once per data frame, which fails to account for and correct changes in loss rates during a single frame. Such changes in loss can occur either when the patient activity changes substantially (such as during a gated cardiac with bolus injection) or when the local external source changes with time (such as a rotating transmission source).

In one embodiment of the invention, deadtime loss information and singles event rates are collected at a time resolution determined by the rate of change in activity. Typically this is approximately 100 milliseconds for the cardiac application and approximately 25 milliseconds for the rotating pin. For cardiac, concurrent with the deadtime and singles data, information is stored on the total slice count. For rotating pin applications, the known pin location is also stored. During image reconstruction the information is available to adjust the quantitative results based on the known local loss, singles rates, and acquisition rates.

Figure 3:
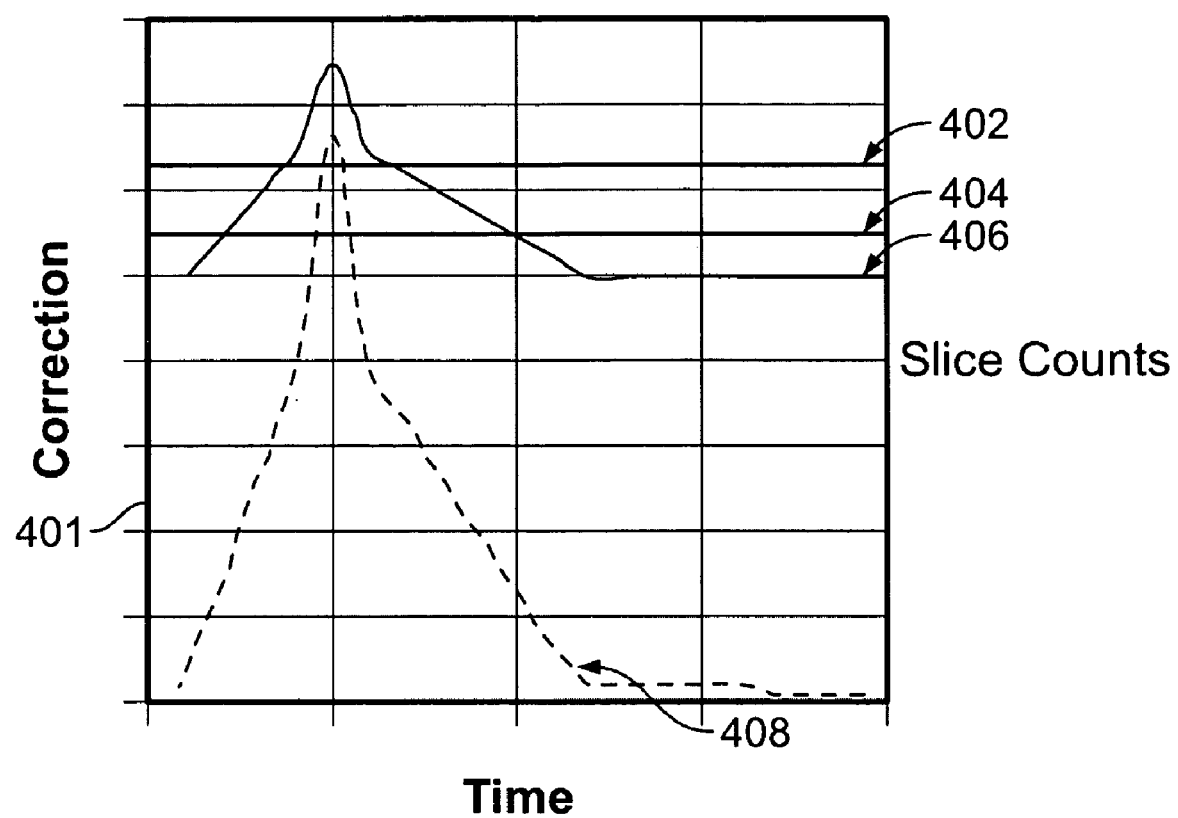
FIG. 3 is an exemplary calculation comparing the correction value for current PET systems with that using the current deadtime correction.

FIG. 3 is an exemplary calculation comparing the correction value for current PET systems with that using deadtime correction in accordance with an embodiment of the present invention. Y axis 401 applies to both the slice counts of the system for both a loss trace 406 and a counts trace 408. The correction factors for a traditional method 404 and deadtime method trace 402 are referred to on Y-axis 401. When, during a short duration of time, the counts changes significantly 408, the current deadtime loss correction factor is calculated in a manner that is proportional to the integrated average of the loss 406. However, the time-resolved correction method will result in a correction value 402 that is significantly more accurate than that used for the traditional average correct 404 method by weighting the loss in short duration of activity and more accurately accounting for the burst activity.

This data rate will not create a substantial burden on the system capability. Data collection requirements are small with respect to the size of image arrays. For example, 280 blocks times 44 bytes of loss values times 10 samples per second equal 123 kbytes per second. This compares to approximately 50 megabytes for the image arrays.

Rapid and time-correlated deadtime loss and/or singles measurements would also allow unique views to be obtained for diagnostic and development reasons.

In many dynamic imaging processes and in particular a PET application, the amount of activity affecting the deadtime of the imaging chain is both dependent on the location in the imaging field and a strong function of time. To compensate for the individual portions of this loss, a sequence of deadtime values is collected with a resolution that is small relative to the rate of change. In the example of cardiac imaging, a time resolution of 100 milliseconds is small relative to the time a bolus of activity takes to move through the heart. During a single 100 millisecond period, the distribution of deadtime contribution between components will also remain essentially constant. If a single value of total counts per slice in the corresponding time period is also retained, then the portion of the entire slice image can be calculated, which provides sufficient information to calculate a deadtime correction sinogram where each element is calculated as the multiplication of the lost correction for each detector element in each time segment. The correction sinogram for the segments are summed in proportion to the counts in that time segment.

Let $\delta_{n,t}$=count rate lost correction factor for detector n during time segment t, and $C_t$=slicecounts in time t The correction sinogram for a single time segment is formed by multiplying the count rate lost correction factor for both detectors contributing to a line of response:

$S^t_{i,k} = \delta_{i,t} \times \delta_{k,t}$

The corrected counts in the sinograms for the time segments is then given by:

$N^t_{i,k} = S^t_{i,k} \times C^t_{i,k}$ where $C^t_{i,k}$ is the measured coincidence counts between crystals i and k during time segment t.

The corrected sinogram for the acquisition is then acquired by summing the corrected sinograms of the time segments, $N_{i,k} = \Sigma S^t_{i,k} \times C^t_{i,k}$.

So long as the coincidence counts between crystals during a time segment are substantially proportionate to the total number of coincidences measured during the segment, $C_{i,k,t} \propto C_t$ the above equation can be simplified as $N_{i,k} = S_{i,k} \times C_{i,k}$ where $C_{i,k}$ is the total number of measured coincidences between crystal i and k during the acquisition, and $$S_{i,k} = \frac{\sum [C_t \times S^t_{i,k}]}{\sum C_t}$$

is the correction sinogram for the acquisition.

The above correction can be extended to the case where random coincidences are present in the data by adding a random correction to the above equations:

$$S_{i,k} = \frac{\sum [(C_t - K_t) \times S^t_{i,k}]}{\sum (C_t - K_t)}$$

$N_{i,k} = S_{i,k} \times (C_{i,k} - K_{i,k})$ where $K_t$ is an estimate of the total number of random coincidences acquired during the time segment t, and $K_{i,k}$ is an estimate of the total number of random coincidences acquired between detector elements j and k for all the time segments. $K_t$ and $K_{i,k}$ are determined using one of the many methods well known in the art. For example, if $R_{n,t}$ is the singles rate for detector element n during time segment t, $T_t$ is the duration of time segment t, and W is the coincidence window width the randoms can be calculated as $K_{i,k} = \sum_t R_{i,t} \times R_{k,t} \times W \times T_t$ and $K_t = \sum_{i,k} R_{i,t} \times R_{k,t} \times W \times T_t$.

The method described above also applies in general to gated acquisitions. Because gated is intrinsically a combination over a long period of time relative to the gate time division, the same correction value would be applied to each gate time.

An alternative method for deadtime correction is to use the block singles rate to scale the contribution for each time segment.

Let $\delta_{n,t}$ equal the count rate lost correction factor and $R_{n,t}$ equal the singles count rate for detector n during time segment t.

The deadtime corrected sinogram element for a coincidence between detector elements i and k is given by:

$S_{i,k} = \Sigma S_{i,k,t} \times \delta_{k,t} \times \delta_{i,t}$.

So long as the coincidence counts between crystals are proportionate to the product of their singles rate, $S_{i,k,t} \propto R_{k,t} \times R_{i,t}$ the equation for the corrected counts in a sinogram element can be re-written as $$S_{i,k} = \Lambda_{i,k} \times \frac{\sum (R_{i,t} \times \delta_{i,t}) \times (R_{k,t} \times \delta_{k,t})}{\sum R_{i,t} \times R_{i,t}},$$

where $\Lambda_{i,k}$ is the uncorrected sinogram.

The sinogram correction factor is then the ratio of the sum of the product of the deadtime corrected block count rates and the sum of the product of the uncorrected block count rates.

In modern PET scanners, the count rate loss of all crystals in a given block are usually equal, and the size of the correction sinograms can be greatly reduced by calculating a block based instead of crystal based correction sinogram.

In the case of attenuation measurement with source pins, there is a substantial loss seen at the detectors near the pin and minimal loss seen by the detectors on the opposite side of the ring. If the average loss rates are used for the correction, then substantial error is seen versus the loss in the useful lines of response.

For each point in the sinogram (blank or attenuation), the pin location and detector pairs that contributed to that location are known. Therefore a table of block loss-rate as a function of pin location is sufficient to calculate the correction that should be applied to each line of response. If required, this correction could be refined using a calculation of the geometric sensitivity for several near locations of the pin.

Because the loss terms are a function of which side of the line of response the pin is currently on, the blank and attenuation sinograms would need to be recorded as near and far sinograms. The loss correction is then applied separately for near and far locations. The near and far sinograms can be applied to produce a normalization correction free of deadtime effects.

The amount of time that the source pin is nominally in front of a given detector is determined by the angle subtended and by the speed of motion of the pin. For a rotation pin of 20 RPM, for example, the pin moves from a position in front of block to a position in front of a subsequent block in 50 milliseconds. Therefore, recording deadtime values every 25 milliseconds is sufficient to record changes due to pin motion.

The deadtime loss of a typical block and singles rates of crystals could be characterized as a function of input count rate. Some forms of component defect (such as excess electronic noise) may be evidenced by a disruption to the expected function. Since both the count rate and loss are recorded for each time segment, correspondence to the expected function can be checked whenever desired. After a base experience is used to define nominal behavior, deviation from the nominal can be flagged as a component defect.

A technical effect of the above described correction methods enable correction for changes in loss rates during a single frame due to changes in patient activity and correction for the number of randoms events in the acquisition by recording singles event rates.

The above-described embodiments of methods and apparatus for correcting errors during data image reconstruction are cost-effective and highly reliable for facilitating image reconstruction when changes in data losses occur when, for example, the patient activity changes substantially, such as, gated cardiac with bolus injection, or when the local external source changes with time, such as, a rotating transmission source. Accordingly, incorporating corrections for randoms and singles into the image reconstruction facilitates, for example, medical diagnostic imaging analysis and diagnosis in a cost-effective and reliable manner.

While the invention has been described in terms of various specific embodiments, those skilled in the art will recognize that the invention can be practiced with modification within the spirit and scope of the claims.

What is claimed is:

1. A method of correcting for deadtime losses in a positron emission tomography (PET) medical imaging device having a plurality of detectors at successive locations circumferentially spaced about a viewing area, said method comprising:
    receiving signals indicative of positron-electron annihilation events occurring along a line of response between pairs of detectors for a plurality of predetermined time segments of data acquisition of said events, each of said predetermined time segments of a duration less than a data frame;
    calculating a deadtime correction sinogram for each predetermined time segment from data acquired during each respective single time segment;
    calculating corrected counts in the deadtime correction sinogram for each time segment;
    combining the corrected counts in the deadtime corrected sinograms to generate an acquisition sinogram; and
    generating an image from the acquisition sinogram.

2. The method in accordance with claim 1 wherein for random coincidence correction said calculating a deadtime correction sinogram for each time segment further comprises calculating a deadtime correction sinogram using an estimate of the total number of random coincidences acquired during each time segment.

3. The method in accordance with claim 1 wherein calculating deadtime correction sinograms comprises acquiring data with a time resolution determined by a rate of change of count activity.

4. The method in accordance with claim 3 wherein calculating deadtime correction sinograms comprises acquiring data for a cardiac application at a time resolution of 100 milliseconds.

5. The method in accordance with claim 1 wherein calculating deadtime correction sinograms comprises acquiring data for a rotating pin application at a time resolution of 25 milliseconds.

6. The method in accordance with claim 1 wherein calculating a deadtime correction sinogram for each line of response comprises recording a deadtime correction sinogram as either near or far matrices, said deadtime correction sinogram being applied to produce a normalization correction free of deadtime effects.

7. The method in accordance with claim 1 further comprising receiving rapid and time correlated deadtime loss data and singles data to generate unique views for at least one of diagnostic and development purposes.

8. The method in accordance with claim 7 wherein receiving rapid and time correlated deadtime loss data and singles data comprises acquiring the deadtime correction data for an amount of time dependent on the angle subtended by the pin and the speed of rotation of the pin.

9. A positron emission system comprising:
    a positron emission tomography scanner;
    at least one pair of opposing detectors spaced about a scanner viewing area;
    a controller for controlling the operation of the positron emission tomography scanner, said controller configured to:
    acquire image data with inherent deadtime losses during a predetermined time segment, said predetermined time segment having a duration of less than a data frame; and
    process the acquired image data during dead time periods, said process including;
    calculating a deadtime correction sinogram for each predetermined time segment from data acquired during each respective single time segment;
    calculating corrected counts in the deadtime correction sinogram for each time segment;
    combining the corrected counts in the deadtime corrected sinogram to generate an acquisition sinogram; and
    generating an image from the acquisition sinogram.

10. The system in accordance with claim 9 wherein, for random coincidence correction said calculating a deadtime correction sinogram for each time segment is further corrected by using an estimate of the total number of random coincidences acquired during each time segment.

11. The system in accordance with claim 9 wherein calculating deadtime correction sinograms comprises acquiring data with a time resolution determined by a rate of change of count activity.

12. The system in accordance with claim 9 wherein calculating deadtime correction sinograms comprises acquiring data for a cardiac application at a time resolution of approximately 100 milliseconds.

13. The system in accordance with claim 9 wherein calculating deadtime correction sinograms comprises acquiring data for a rotating pin application at a time resolution of approximately 25 milliseconds.

14. The system in accordance with claim 9 wherein calculating a deadtime correction sinogram for each line of response comprises recording a deadtime correction sinogram as either near or far matrices, said deadtime correction sinogram being applied to produce a normalization correction free of deadtime effects.

15. The system in accordance with claim 9 further comprising receiving rapid and time correlated deadtime loss data and singles data to generate unique views for at least one of diagnostic and development purposes.

16. The system in accordance with claim 15 wherein receiving rapid and time correlated deadtime loss data and singles data comprises acquiring the deadtime correction data for an amount of time dependent on the angle subtended by the pin and the speed of rotation of the pin.

17. A computer program embodied on a computer readable medium for controlling a positron emission tomography (PET) system comprising a code segment configured to control the PET system to reduce deadtime losses by calculating a deadtime correction sinogram for each time segment of a detector channel of the positron emission system, said computer program;
    receives emission data indicative of positron electron annihilation events during a predetermined time segment of a duration less than a data frame;
    calculates a deadtime correction sinogram for each predetermined time segment from data acquired during each respective single time segment;
    calculates corrected counts in the deadtime correction sinogram for each time segment;
    combines the corrected counts in the deadtime corrected sinogram to generate an acquisition sinogram; and
    generates an image from the acquisition sinogram.

18. The computer program in accordance with claim 17 wherein for random coincidence correction said calculating a deadtime correction sinogram for each time segment is further corrected by using an estimate of the total number of random coincidences acquired during each time segment.

19. The computer program in accordance with claim 17 that calculates deadtime correction sinograms from data acquired with a time resolution determined by a rate of change of count activity.

20. The computer program in accordance with claim 17 that calculates deadtime correction sinograms using data acquired for a cardiac application at a time resolution of approximately 100 milliseconds.

21. The computer program in accordance with claim 17 that calculates deadtime correction sinograms using data acquired for a rotating pin application at a lime resolution of approximately 25 milliseconds.

22. The computer program in accordance with claim 21 that comprises acquiring deadtime correction data for an amount of time dependent on the angle subtended by the pin and the speed of rotation of the pin.

23. The computer program in accordance with claim 17 that calculates a deadtime correction sinogram for each line of response from data recorded as a deadtime correction sinogram as either near or far matrices, said deadtime correction sinogram being applied to produce a normalization correction free of deadtime effects.

24. The computer program in accordance with claim 17 that generates unique views for at least one of diagnostic and development purposes.

* * * * *